United States Patent [19]

Hashiguchi et al.

[11] Patent Number: 4,779,613
[45] Date of Patent: Oct. 25, 1988

[54] ENDOSCOPE WITH MEANS FOR PREVENTING AN OBSERVING OPTICAL SYSTEM FROM BEING FOGGED

[75] Inventors: Toshihiko Hashiguchi, Sagamihara; Hiroyuki Kusunoki, Higashimurayama; Shozo Shibuya, Hachioji, all of Japan

[73] Assignee: Olympus Optical Co., Ltd., Tokyo, Japan

[21] Appl. No.: 25,293

[22] Filed: Mar. 12, 1987

[30] Foreign Application Priority Data

Mar. 13, 1986 [JP] Japan .................................. 61-056187
Mar. 13, 1986 [JP] Japan .................................. 61-056188

[51] Int. Cl.⁴ .............................................. A61B 1/06
[52] U.S. Cl. ........................................ 128/6; 350/589
[58] Field of Search ................. 128/4, 6; 604/358; 350/589

[56] References Cited

U.S. PATENT DOCUMENTS

| | | | |
|---|---|---|---|
| 2,184,352 | 12/1939 | Langsner | 350/589 |
| 2,421,805 | 6/1947 | Peck | 350/589 |
| 3,740,114 | 6/1973 | Thompson | 350/589 |
| 4,036,218 | 7/1977 | Yamashita et al. | 128/4 |
| 4,341,205 | 7/1982 | Hosono et al. | 128/6 |
| 4,538,593 | 9/1985 | Ishii | 128/4 |

FOREIGN PATENT DOCUMENTS

| | | |
|---|---|---|
| 2062178 | 6/1972 | Fed. Rep. of Germany . |
| 3307185 | 9/1983 | Fed. Rep. of Germany . |
| 59-7422 | 1/1984 | Japan . |
| 59-194722 | 12/1984 | Japan . |
| 60-165614 | 8/1985 | Japan . |
| 60-186420 | 12/1985 | Japan . |

*Primary Examiner*—William H. Grieb
*Attorney, Agent, or Firm*—Armstrong, Nikaido, Marmelstein & Kubovcik

[57] ABSTRACT

This endoscope is provided within an endoscope body having an elongate insertion part having an observing window at the tip and an operating part provided as connected to the rear end of this insertion part with an observing optical system transmitting an observed image from the tip of the above mentioned insertion part to the above mentioned operating part and is provided with a first airtightening device for making the above mentioned endoscope body airtight in the structure and a second airtightening device for making at least a part of the above mentioned observing optical system airtight in the structure or is provided within the above mentioned endoscope body with a hygroscopic member formed of a flexible sheet-shaped hygroscopic material.

26 Claims, 15 Drawing Sheets

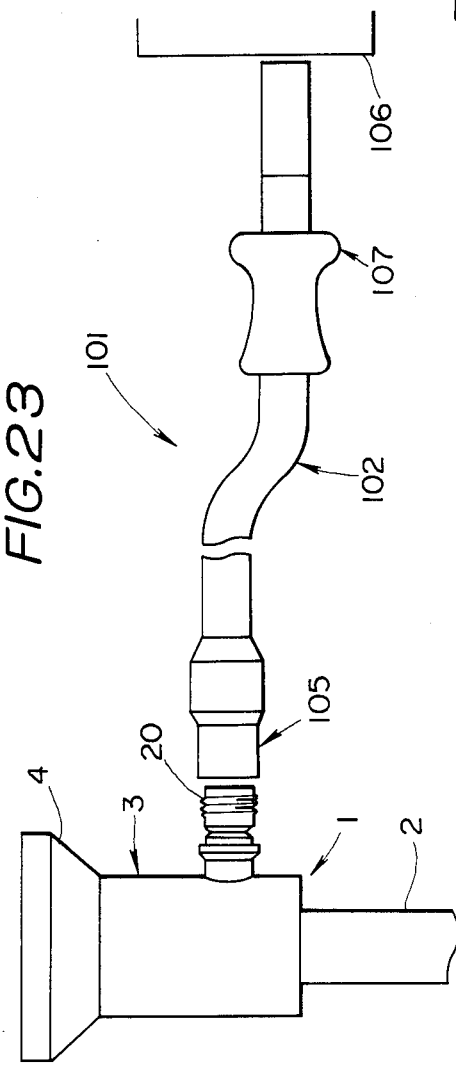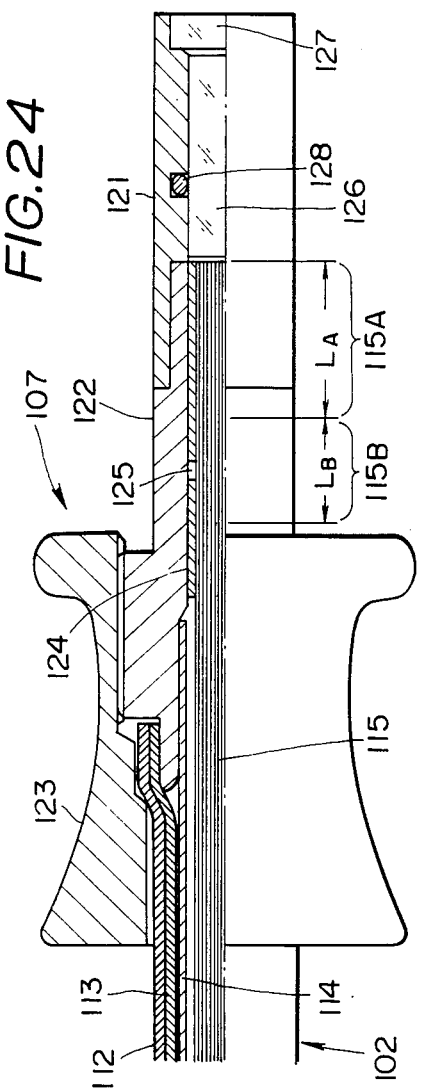

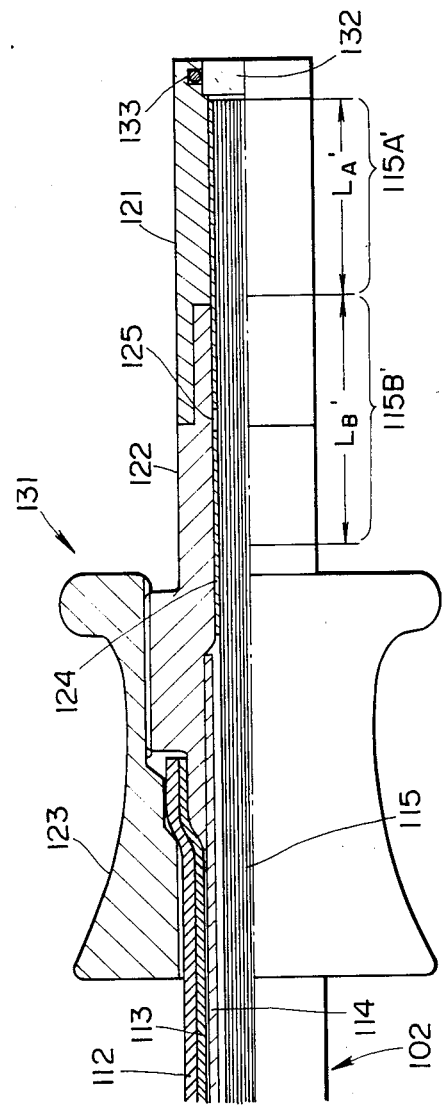
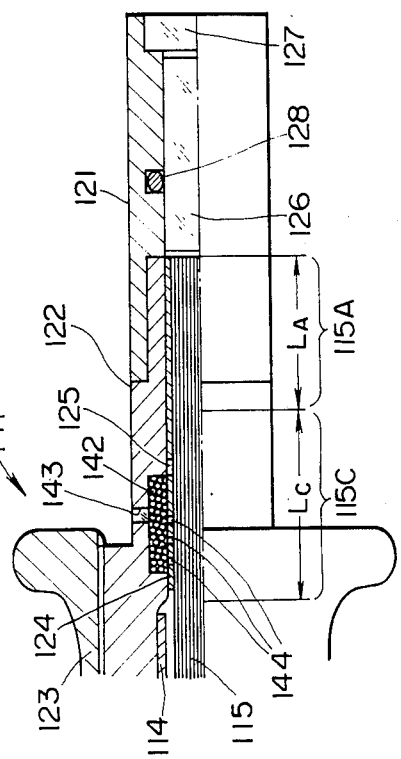

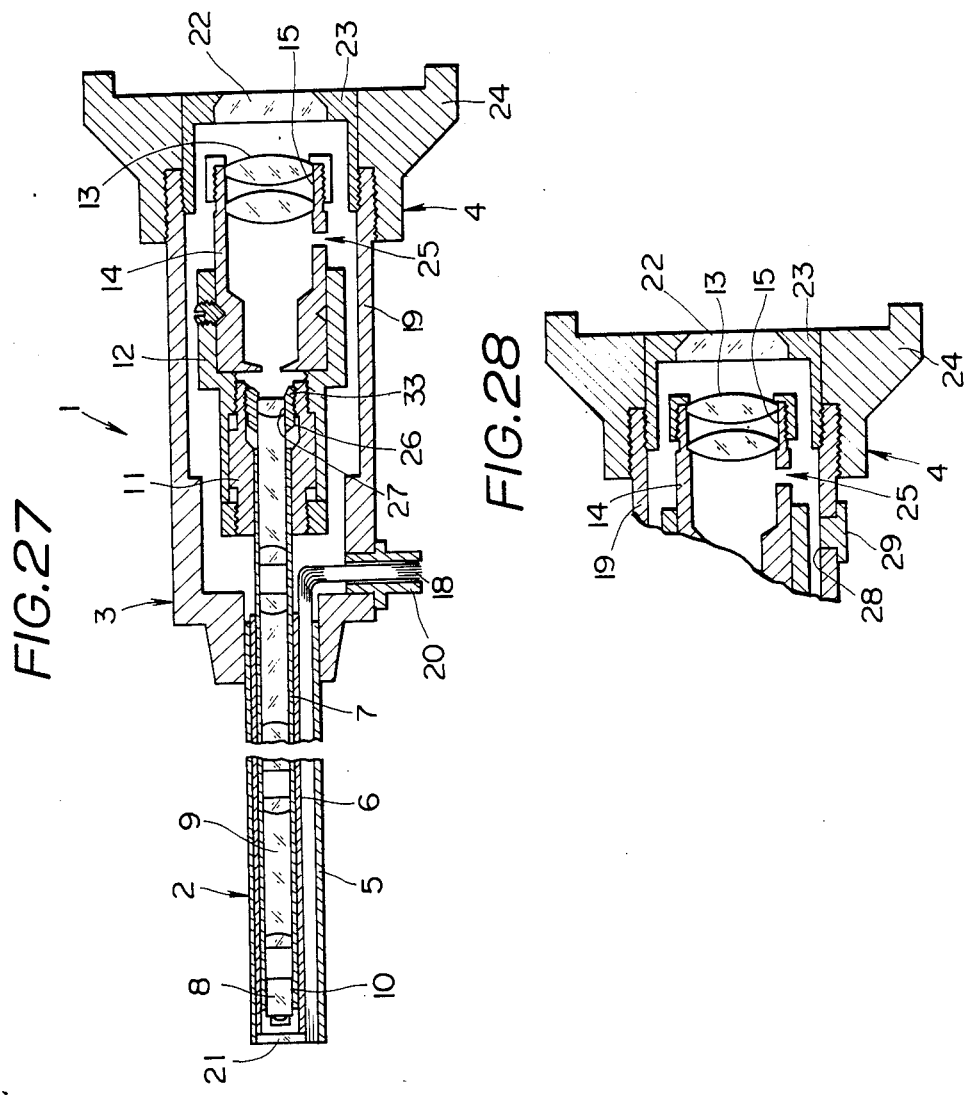

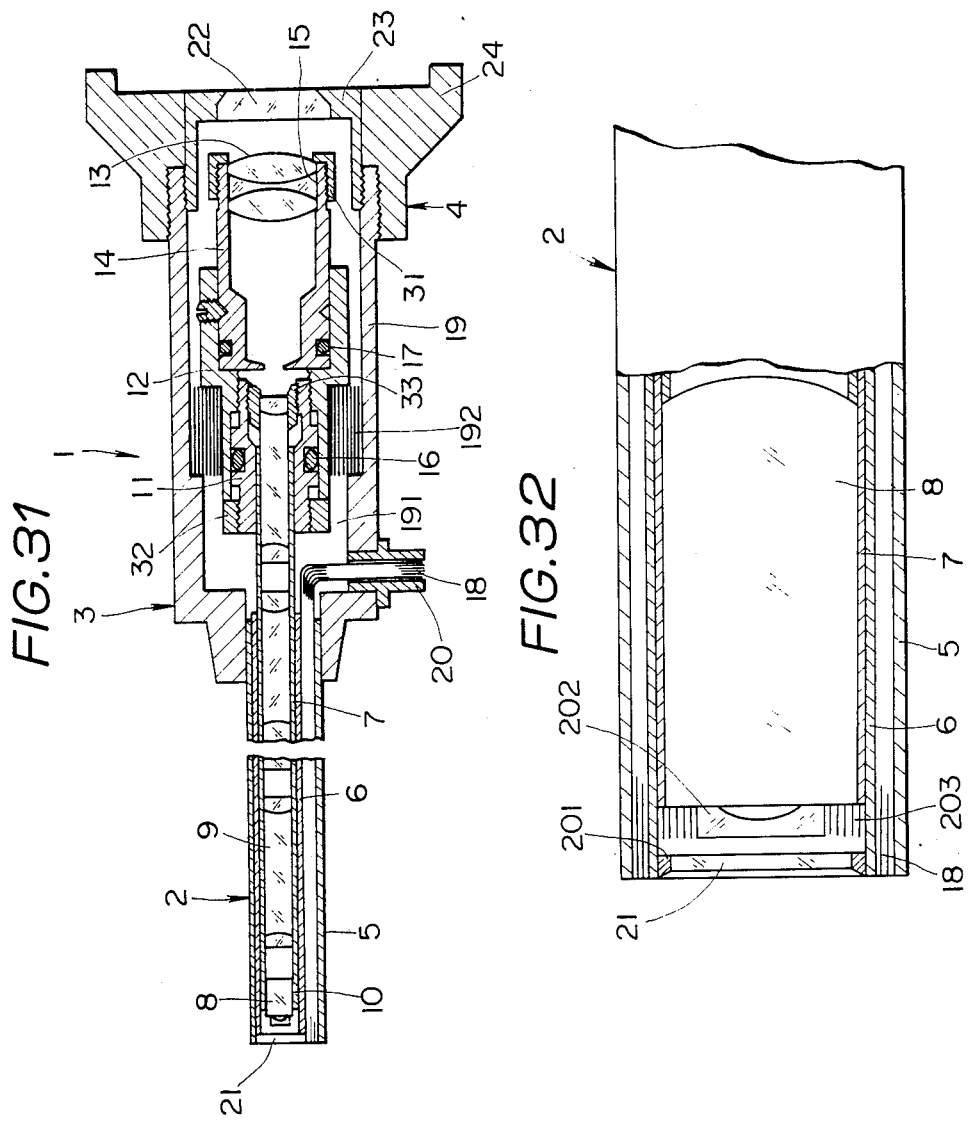

4,779,613

ENDOSCOPE WITH MEANS FOR PREVENTING AN OBSERVING OPTICAL SYSTEM FROM BEING FOGGED

BACKGROUND OF THE INVENTION

1. Field of the Invention

This invention relates to an endoscope wherein the observing optical system can be prevented from being fogged.

2. Related Art Statement

Recently, an endoscope has come to be extensively used to observe a body cavity or the like or treat the same with treating tools by inserting the elongate insertion part into the body cavity or the like.

However, the endoscope to be used within the body cavity or the like must be used in a physiological saline solution or must be sterilized with a chemical solution and is therefore made of such waterproof and airtight structure as is shown, for example, in the gazette of Japanese Utility Model Laid Open No. 194722/1984 or the specification of West German Patent Laid Open No. 2062178.

Now, the conventional endoscope is made waterproof and airtight only in the outside fitting part. Therefore, the slightest amount of a water vapor entering the interior of the endoscope from outside will reach the interior of the observing optical system and will condense and fog the inside surface of the objective or the like and the observation will not be possible. Particularly, in the high pressure steam sterilization considered to be the most effective sterilization, a high temperature high pressure water vapor is used and a slight amount of the water vapor is very likely to enter the endoscope body even if the outside fitting is made.

By the way, in the gazette of Japanese Utility Model Laid Open No. 186420/1985, there is disclosed an endoscope wherein a moistureproof member made of a highly hygroscopic material is provided inside the endoscope body of a liquidtight structure.

Such hygroscopic material as slaked lime and active carbon shown in the above mentioned related art example and as silicagel and calcium carbonate are granular or powdery and are difficult to mold in the form of the interior of the endoscope. The moistureproof member formed of such hygroscopic material is likely to be broken and, in case it is broken, the observation will be likely to be obstructed by its fragments.

OBJECTS AND SUMMARY OF THE INVENTION

An object of the present invention is to provide an endoscope wherein the observing optical system can be prevented from being fogged and obstructing the observation.

Another object of the present invention is to provide an endoscope wherein an observation will not be obstructed by materials resulting from breakage of the hygroscopic member.

According to the present invention, an endoscope is provided within an endoscope body having an elongate insertion part having an observation window at the tip and an operating part connected to the rear end of the insertion part with an observing optical system transmitting an observed image from the tip of the above mentioned insertion part to the above mentioned operating part and is provided with a first airtightening means making the above mentioned endoscope body airtight in the structure and a second airtightening means making at least a part of the above mentioned observing optical system airtight in the structure or is provided within the above mentioned endoscope body with a hygroscopic member formed of a flexible sheet-shaped hygroscopic material.

The other features and advantages of the present invention will become apparent with the following explanation.

BRIEF DESCRIPTION OF THE DRAWINGS

FIG. 2 is a sectional view of an endoscope of a modified example.

FIG. 3 is a sectional view showing the eyepiece cover glass surroundings of the endoscope in FIG. 2.

FIGS. 4, 5 and 6 are sectional views showing the eyepiece cover glass surroundings of respectively further other modified examples.

FIG. 9 is a sectional view showing the incident end surroundings of the light guide.

FIG. 10 is an explanatory view showing a step in the course of fixing the light guide by using a mouthpiece.

FIG. 11 is a sectional view showing the incident end surroundings of the light guide using a mouthpiece different from that in FIG. 9.

FIG. 12 is a sectional view showing the tip part of a perspective view type rigid endoscope.

FIG. 13 is a sectional view showing the eyepiece part surroundings.

FIG. 14 is a side view partly in section showing the incident end surroundings of a light guide.

FIG. 15 is a sectional view showing the incident end surrounding of a light guide.

FIG. 16 is a sectional view showing the tip part of an endoscope.

FIG. 17 is an elevation of FIG. 16.

FIG. 18 is a sectional view of an endoscope of a modification example.

FIGS. 19 to 22 are sectional views each showing a cementing part of an operating part body with an outer tube of another modified example.

FIGS. 23 to 26 show some examples of a light guide cable to be connected to an endoscope to which the present invention is applied.

FIG. 23 is a side view of a light guide cable.

FIG. 24 is a sectional view showing a light source side connector part.

FIG. 25 is a sectional view showing a light source side connector part of another example.

FIG. 26 is a sectional view showing a part of a light source side connector part of further another example.

FIG. 27 is a sectional view of an endoscope of the second embodiment of the present invention.

FIG. 28 is a sectional view of the rear end side of an operating part, showing a modified example of the second embodiment.

FIG. 29 is a side view of a flexible endoscope.

FIG. 30 is a sectional view of a tip part of an insertion part.

FIG. 31 is a sectional view of an endoscope of the fourth embodiment of the present invention.

FIG. 32 is a view partly in section showing a tip part of an insertion part of an endoscope relating to the fifth embodiment of the present invention.

DETAILED DESCRIPTION OF THE PREFERRED EMBODIMENTS

Figure 1:
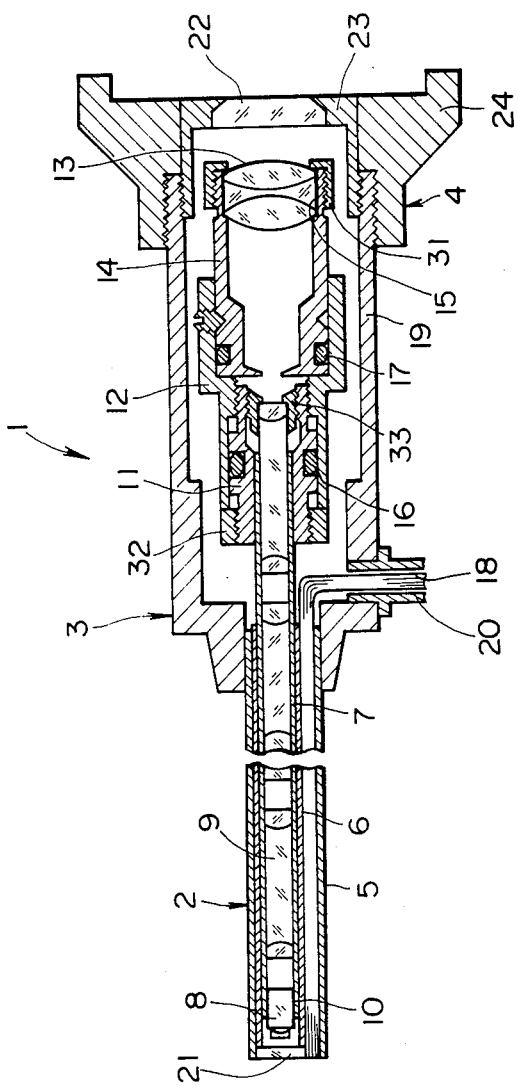
FIG. 1 is a sectional view of an endoscope of the first embodiment of the present invention.

FIG. 1 shows the first embodiment of the present invention.

A rigid endoscope 1 is formed of a rigid small diameter insertion part 2, a large diameter operating part secured to the rear end of the insertion part 2 so as to be kept airtight and an eyepiece part 4 connected to the rear end of the operating part 3.

An inner tube 6 is inserted eccentrically on the upper side through an outer tube 5 forming the above mentioned insertion part 2. Further, a system tube 7 extended into the above mentioned operating part 3 is inserted through this inner tube 6. An objective 8 and relay lens 9 are internally fitted from the tip side within this system tube 7. The above mentioned objective 8 in contact on the outer peripheral surface with the inner peripheral surface of the system tube 7 is cemented to the system tube with a cement 10 so as to be kept airtight between the objective 8 and system tube 7.

A relay lens frame 11 is secured so as to be kept airtight on the rear end side of this system tube 7, is screwed to a connecting tube 12 and is connected through this connecting tube 12 to an eyepiece frame 14 containing an eyepiece 13. This eyepiece 13 is fitted in from the rear of the eyepiece frame 14 and is cemented on the entire peripheral surface to the eyepiece frame 14 with a cement 15 so as to be kept airtight between the eyepiece 13 and eyepiece frame 14. This eyepiece 13 is prevented from being pulled out by a lens presser 31 in contact with the rear end peripheral edge of the eyepiece.

The rear side of the above mentioned connecting tube 12 is expanded in diameter. The eyepiece frame 14 is fitted into the expanded rear side of the connecting tube 12 and then a screw is screwed in from the connecting tube 12 side and is engaged and fixed in a V-shaped peripheral groove of the eyepiece frame 14. By the way, the fitted screw part is connected with a cement. By rotating the connecting tube 12, the connecting tube 12 fixing position can be adjusted by being moved forward and rearward along the optical axis direction of the relay lens system 9 with respect to the relay lens frame 11. The eyepiece 13 is adjusted in the proper position with respect to the relay lens system 9 and then can be fixed in the adjusted position with a nut 32 screwed to a male thread on the outer periphery of the front end of the relay lens frame 11. By the way, the lens of the final step of the relay lens system 9 is fixed by a relay lens presser 33.

By the way, O-rings 16 and 17 made of a fluorine-based rubber are arranged respectively between the above mentioned relay lens frame 11 and connecting tube 12 and between the connecting tube 12 and eyepiece frame 14 so as to be kept airtight.

A substantially tubular operating part body 19 containing the above mentioned relay lens frame 11, connecting tube 12 and eyepiece frame 14 is externally fitted at the front end to the rear end of the above mentioned outer tube 5 and is secured with a cement so as to be kept airtight.

On the other hand, light guide fibers 18 are inserted as an illuminating light transmitting means between the outer tube 5 and inner tube 6 within the above mentioned insertion part 2, are bent on the base side within the operating part 3 and are extended out to a light guide mouthpiece 20 provided on the side of the above mentioned operating part body 19.

By the way, clearances are filled with a cement at both ends of the above mentioned light guide fibers 18 so as to be kept airtight.

At the tip of the above mentioned inner tube 6, an objective cover glass 21 is secured on the peripheral edge with a cement so as to be kept airtight. On the other hand, at the rear end of the above mentioned operating part body 19, an eyepiece cover glass frame 13 holding an eyepiece cover glass 22 is secured on the peripheral edge with a cement so as to be kept airtight.

Also, between the operating part body 19 and eyepiece cover glass frame 23, airtightness is kept with a cement or the like.

An eyepiece cover glass frame holder 24 is fitted to the rear end of the above mentioned operating part body 19 and the outer peripheral part of the eyepiece cover glass frame 23.

In the first embodiment formed as in the above, the endoscope 1 is made airtight in the outer fitting with a cement or the like and further the observing optical system from the objective 8 to the eyepiece 13 is also made airtight with cements 10 and 15 and O-rings 16 and 17. Even if the eyepiece 13 is moved forward and rearward, for example, to adjust the focus, this observing optical system will be kept airtight by the O-rings 16 and 17.

Therefore, in case the endoscope 1 is sterilized by the high pressure steam sterilizing method, even if the water vapor enters the interior of the endoscope 1 or, for example, the interior of the operating part body 19 through the respective cementing parts on the outer surface of the endoscope 1, this water vapor will be prevented from entering the above mentioned observing optical system. Therefore, the observing optical system will not be fogged to obstruct the observation. Even in case the water vapor enters the interior of the endoscope 1, this water vapor will not reach the interior of the observing optical system and therefore the repair will be simple.

By the way, between the relay lens frame 11 and connecting tube 12 and between the connecting tube 12 and eyepiece frame 14, airtightness may be kept by a silicone-based or epoxy-based cement instead of the O-rings 16 and 17. When the above mentioned relay lens frame 11, connecting tube 12 and eyepiece frame 14 are fixed with the cement, the assembling work will be simple and the observing optical system will be little deranged under the influence of the vibration or the like from outside.

Also, the above mentioned relay lens frame 11, connecting tube 12 and eyepiece frame 14 may be of an integral structure instead of respectively different members. In such case, the assembling work will be simpler and airtightness will be higher.

FIGS. 2 to 6 show some modified examples of the surroundings of the eyepiece cover glass of the endoscope to which the present invention is applied.

Figure 2:
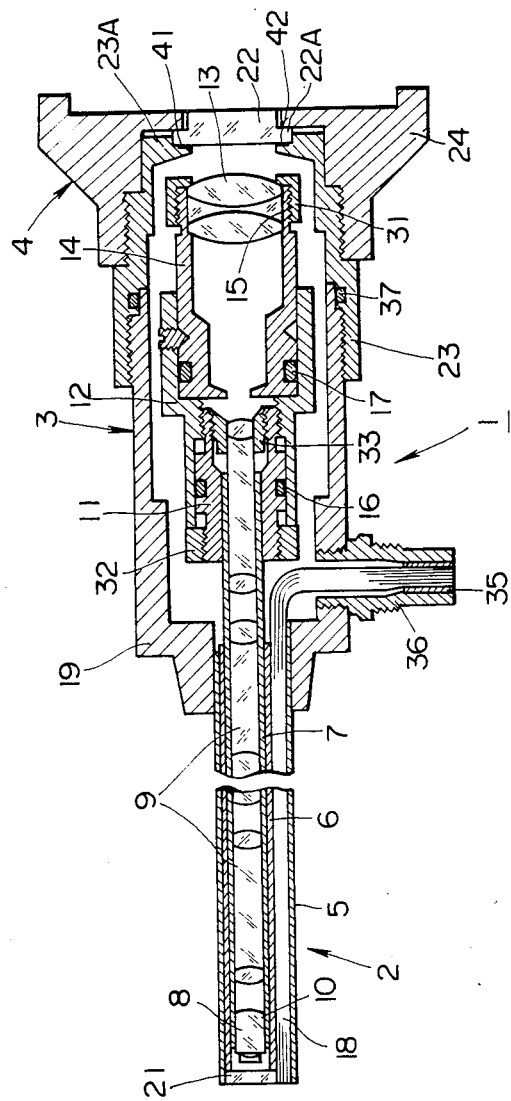
FIGS. 2 to 6 show some modifications of the eyepiece cover glass surroundings of an endoscope to which the present invention is applied.
Figure 3:
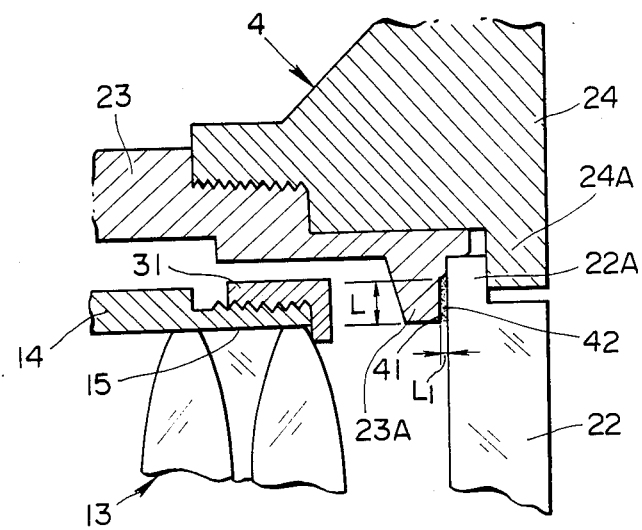

In the example shown in FIGS. 2 and 3, the light guide fibers 18 are fixed on the base side to a light guide mouthpiece 35 which is fixed by pressing or cementing to a mouthpiece supporting frame 36 screwed to the side of the operating part body 19.

The eyepiece cover glass frame 23 fitted with the eyepiece cover glass 22 is screwed to the rear end part of the operating part body 19. An O-ring 37 is fitted around the fitting part of the above mentioned operating part body 19 with the eyepiece cover glass frame 23 so as to keep the structure airtight.

The above mentioned eyepiece cover glass 22 is secured by such fitting structure as is shown in FIG. 3.

That is to say, a flange part 22A is formed on the inside surface of the eyepiece cover glass 22. On the other hand, the eyepiece cover glass frame 23 is provided at the rear end with a flange part 23A projecting inward in the radial direction. An incised recess into which the flange part 22A of the eyepiece cover glass 22 can be fitted is formed in this flange part 23A. In the part opposed to the peripheral edge of the front surface (inside surface) of the eyepiece cover glass 22 in this incised recess, the inner peripheral side part is incised in the form of a step with a width $L_1$, for example, of about 0.1 mm. to form an air gap part 41 so that the eyepiece cover glass 22 may be airtightly secured by filling this air gap 41 with a cement 42. Thus, in a high temperature and high pressure environment, even in case the thermal expansion coefficients of the cover glass 22 and cover glass frame 23 are different from each other, the cement 42 will be able to function as a buffer to prevent the cementing part from peeling off. By the way, it is effective that the width L of the step of the above mentioned air gap part 41 is about 0.5 to 5% of the outside diameter of the eyepiece cover glass 22.

A material whose thermal expansion coefficient as solidified is between the thermal expansion coefficients of the cover glass 22 and cover glass frame 23 is preferable as the above mentioned cement 42. It is more effective to use a substance having an elasticity or high adhesion as solidified.

The flange part 22A of the above mentioned cover glass 22 is pressed and fixed on the rear surface side by the projecting edge part 23A of the eyepiece part 24.

Thus, in the modified example, the eyepiece cover glass frame 23 fitted with the eyepiece cover glass 22 is provided with the air gap part 41 and is secured by filling the air gap part 41 with the cement 42 so as to form a layer-shaped cement 42 part between the cover glass 22 and cover glass frame 23. Therefore, in case the endoscope 1 is exposed to a high temperature high pressure water vapor as in the case of being sterilized by the high pressure steam sterilizing method, even if the eyepiece cover glass 22 and eyepiece cover glass frame 23 are deformed by the different thermal expansion coefficients, the cement 42 in the air gap part 41 will act as a buffer to effectively prevent the eyepiece cover glass 22 and eyepiece cover glass frame 23 from separating from each other to allow the water vapor to enter the endoscope 1.

Figure 4:
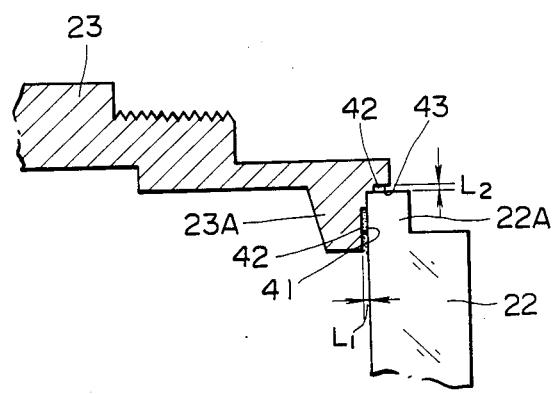
Figure 5:
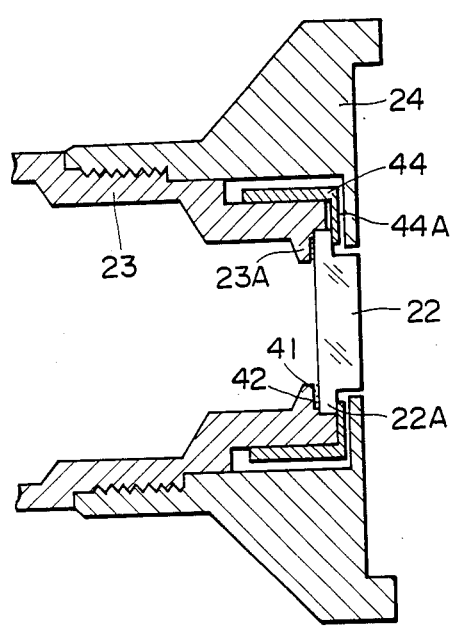
Figure 6:
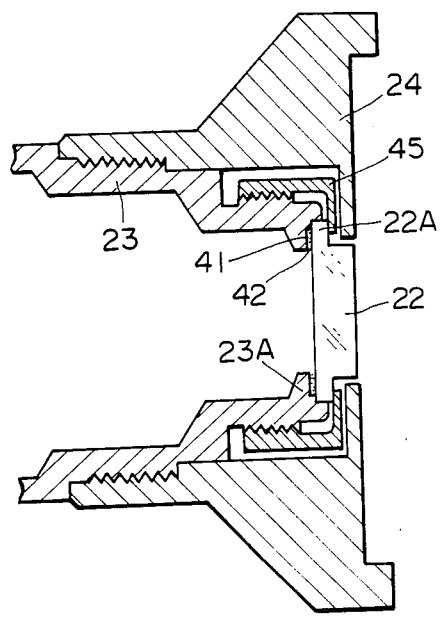

The above mentioned eyepiece cover glass 22 may be secured in such fitting structure as is shown in FIGS. 4 to 6.

That is to say, in the example shown in FIG. 4, an air gap part 43, for example, of a width $L_2$ is provided also in the inner peripheral part at the rear end of the eyepiece cover glass frame 23 in contact with the outer peripheral side of the flange part 22A of the eyepiece cover glass 22 so as to fix the cover glass 22 by filling this air gap part 43 with the cement 42. According to this example, the difference between the thermal expansion coefficients of the eyepiece cover glass 22 and eyepiece cover glass frame 23 in the outer peripheral direction can be effectively coped with.

In the example shown in FIG. 5, the flange part 22A of the eyepiece cover glass 22 is not pressed on the rear side by the projecting edge part 24A of the eyepiece part 24 as in the example shown in FIG. 3 but is pressed an held by a projecting edge part 44A at the rear end of an eyepiece cover glass pressing frame 44 into which the eyepiece cover glass frame 23 is pressed on the outer periphery at the rear end.

This example has substantially the same functions and effects as the above mentioned example shown in FIG. 3.

In the example shown in FIG. 6, instead of the cover glass pressing frame 44 in the example in FIG. 5, there is used an eyepiece cover glass pressing frame 45 in which is formed a female screw threaded to a male screw on the outer periphery at the rear end of the eyepiece cover glass frame 23 so as to press the eyepiece cover glass 22.

This example has substantially the same functions and effects as the example shown in FIG. 2 or 5 and can be applied to the example shown in FIG. 4.

Figure 7:
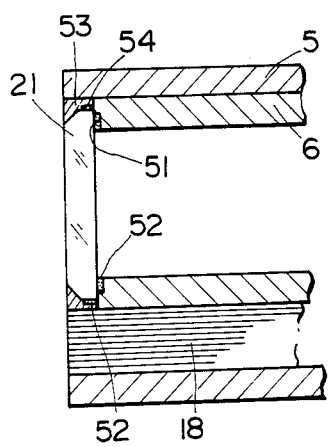
FIGS. 7 and 8 are sectional views showing two modified examples of the objective cover glass surroundings of an endoscope to which the present invention is applied.
Figure 8:
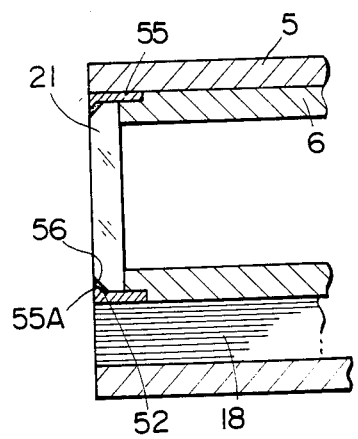

Further modified examples of the fitting structure and the objective cover glass 21 are shown in FIG. 7 or 8.

In the example shown in FIG. 7, the inner tube 6 inserted through the outer tube 5 is incised on the inside diamete side at the front end to form an air gap part 51 filled with a cement 52 and the objective cover glass 21 is secured on the inside surface to the front end of the inner tube 6. Also, an objective cover glass frame 53 opposed to the outer periphery of the objective cover glass 21 is incised on a part of the inner periphery to form an air gap part 54 filled with the cement 52 so that the objective cover glass 21 may be secured. By the way, the objective cover glass frame 53 if fixed with a cement or the like in the part opposed to the front end surface of the inner tube 6 or is secured with a cement or the like on the outer peripheral part.

This example has the same functions and effects as the examples shown in the above mentioned FIGS. 3 and 4.

In the example shown in FIG. 8, the objective cover glass frame 53 in the example shown in the above mentioned FIG. 7 is extended on the rear end side so that a cover glass frame 55 may be pressed or cemented into the incision on the outer periphery at the front end of the inner tube 6 (or may be screwed instead of being pressed in).

In this example, the flange part 55A of the objective cover glass frame 55 in the part opposed to the tapered part of the peripheral edge of the front part of the objective cover glass 21 is provided with an air gap part 56 filled with cement 52 so as to be fixed.

By the way, in the present invention, the above described various modified examples may be combined and the eyepiece cover glass side fitting mechanism may be applied to the objective cover glass side fitting mechanism or vice versa. Also, the objective cover glass may be made concave lens-shaped or convex lens-shaped or the eyepiece cover glass may be made lens-shaped.

Figure 9:
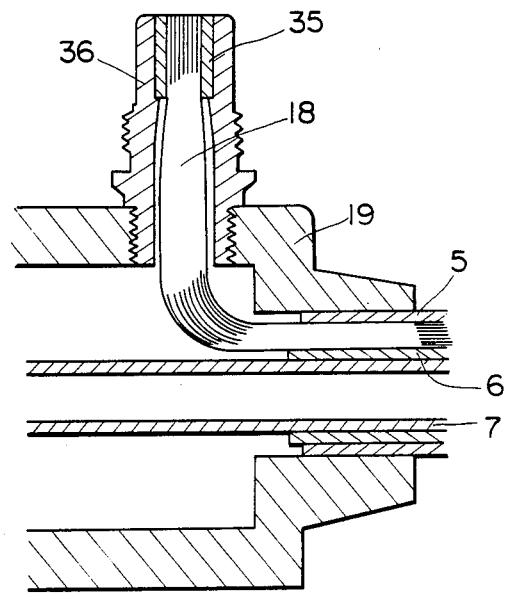
FIGS. 9 to 11 show modified examples of the incident end of the light guide of an endoscope to which the present invention is applied.
Figure 10:
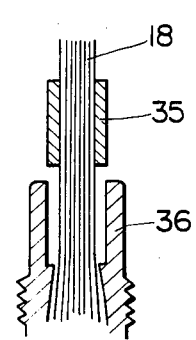
Figure 11:
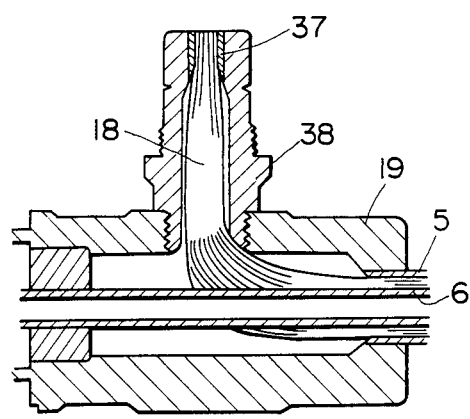

FIGS. 9 to 11 show modified examples of the incident end of the light guide of the endoscope to which the present invention is applied.

The light guide holding side fixing mechanism in the endoscope 1 can be made in such structure as is shown in FIG. 9.

That is to say, the light guide 18 is pressed and fixed at the illuminating light incident end into the mouthpiece supporting frame 36 through the light guide mouthpiece 35.

In the case of fixing the above mentioned light guide 18 through the mouthpiece 35, as shown in FIG. 10, the light guide 18 is passed through the mouthpiece supporting frame 36, then the mouthpiece 35 bundling the light guide 18 is moved downward and is pressed or cemented into the mouthpiece supporting frame 36, the light guide 18 projecting out of the mouthpiece 35 and supporting frame 36 is cut off on the end surface and the cut surface may be ground. In the conventional example in which the light guide 18 is fixed directly to the supporting frame 36 without using the mouthpiece 35, the inside diameter of the supporting frame 36 must be made so small (as to be about the inside diameter of the above mentioned mouthpiece 35) and, in the case of inserting the light guide 18, it will be likely to be broken. However, according to this example, the light guide 18 can be prevented from being broken. That is to say, if the mouthpiece 35 and mouthpiece supporting frame (mouthpiece fitting frame) 36 are used, the light guide 18 will be able to be easily secured at the incident end without being broken.

By the way, in the above explanation, the mouthpiece 35 is moved. The light guide 18 may also be moved together with the mouthpiece 35. In such case, the light guide 18 may be pulled from the insertion part tip side.

By the way, the light guide mouthpiece is not limited to be the above described one but may be a mouthpiece 37 in which, as shown in FIG. 11, the end part on the side expanded in the diameter to be tapered of the supporting frame 38 is made an end surface incised to be tapered. By the way, in FIG. 11, the operating part body 19 is of a structure different from that shown in FIG. 2 or 9. In FIG. 11, the light guide 18 is inserted through the air gap outside the inner tube 6 concentric with the outer tube 5. A system tube (not illustrated) is also contained within this inner tube 6.

By the way, in the endoscope to which the present invention is applied, the cover glass closing the window part facing the outer surface of at least one optical system of the illuminating optical system and observing optical system may be formed of borosilicate glass.

For example, in FIG. 1, both objective cover glass 21 and eyepiece cover glass 22 may be formed of borosilicate glass (called Pyrex glass).

This borosilicate glass is preferably composed substantially of 80% $SiO_2$, 2% $Al_2O_3$, 13% $B_2O_3$ and less than 5% $Na_2O$. This material is waterproof, is highly heatproof and is endurable to a high temperature high pressure water vapor. For example, the high temperature high pressure water vapor sterilization is conducted at about 132° to 135° C. which this material will easily endure. Therefore, when the objective cover glass 21 and eyepiece cover glass 22 closing the respective window parts facing the outside of the observing optical system are made of borosilicate glass, even if they are treated to be sterilized with the above mentioned water vapor, the cover glass surfaces will be prevented from deteriorating and fogging.

FIGS. 12 to 17 show some further modified examples of the cover glass of the endoscope to which the present invention is applied.

Figure 12:
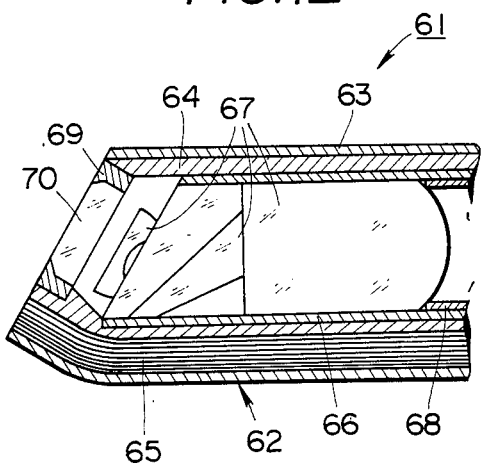
FIGS. 12 to 17 show some modification examples of a cover glass of en endoscope to which the present invention is applied.

FIG. 12 shows an example of a perspective view type rigid endoscope.

An outer tube 63 forming an insertion part 62 of this endoscope is bent forwardly upward in the bottom part on the tip side and is obliquely cut on the bottom side so that the bent part may remain. An inner tube 64 is inserted through this outer tube 63 eccentrically so as to contact the upper end of the inner periphery, is also bent forwardly upward in the bottom part on the front end side and is obliquely cut. A light guide 65 is inserted through the meniscus-shaped air gap part between the outer periphery of this inner tube 64 and the inner periphery of the outer tube 63. A lens tube 66 is inserted through the above mentioned inner tube 64 and an objective 67 is arranged on the tip side of this lens tube 66 and is secured to the inner peripheral surface of the lens tube 66 with a cement. In the rear of this lens tube 66, a relay lens system not illustrated is contained and secured through a spacer 68.

Now, in front of the optical axis of the front lens of the above mentioned objective 67, an objective cover glass 70 is secured through a cover glass frame 69. This objective cover glass 70 is fitted on the outer peripheral surface onto the inner peripheral surface of a cover glass frame 69 and is secured with a cement. This cover glass frame 69 to which the cover glass 70 is positively secured is secured by cementing or soldering to the inner peripheral surface at the front end of the inner tube 64. By the way, the objective cover glass 70 is incised to be tapered on the peripheral edge of the front surface. On the other hand, the cover glass frame 69 into which this objective cover glass 70 is fitted is provided with a flange part projecting inward in the diametral direction in the part opposed to the above mentioned incision. Therefore, when the objective cover glass 70 is secured with this cover glass frame 69, the objective cover glass 70 will be prevented from escaping and dropping during the use or the like. (By the way, the objective cover glass 70 may be incised on the peripheral edges of both surfaces of the objective cover glass 70 and the cover glass frame 69 may be provided with flange parts corresponding to both of the above mentioned incisions.)

The above mentioned objective cover glass 70 is made of borosilicate glass.

In this example, the cover glass fitting structure is different from that of the example shown in FIG. 1 but the action on the sterilizing treatment with a high temperature high pressure water vapor is the same as in the case of using the borosilicate glass for the objective cover glass 21 in FIG. 1.

Figure 13:
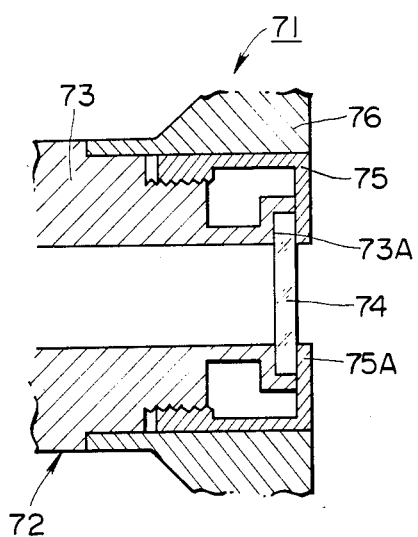

In the example shown in FIG. 13, in an endoscope 71, for example, a recess 73A for containing an eyepiece cover glass 74 is formed at the rear end of an operating part body 73 forming an operating part 72 and the eyepiece cover glass 74 is fitted in this recess 73A. The eyepiece cover glass 74 in this fitted part is secured on the peripheral edge of the inside surface and the outer peripheral surface with a cement or the like. The operating part body 73 positioned before the securing position of this eyepiece cover glass 74 is made steppedly smaller in the diameter on the outer periphery and has a male screw part formed thereon. A cover glass presser 75 having a female screw formed on the inner periphery is screwed to this male screw part and is formed at the rear end as flange part 75A projecting radially inward. The eyepiece cover glass 74 is pressed on the peripheral edge of the outside surface with this flange part 75A so as to be able to be prevented from escaping and dropping. By the way, an eyepiece part 76 is fitted to the outer periphery of this cover glass presser 75.

In this example, too, the eyepiece cover glass 74 is made of borosilicate glass and therefore has the same resistance to the high temperature high pressure water vapor sterilization.

Figure 14:
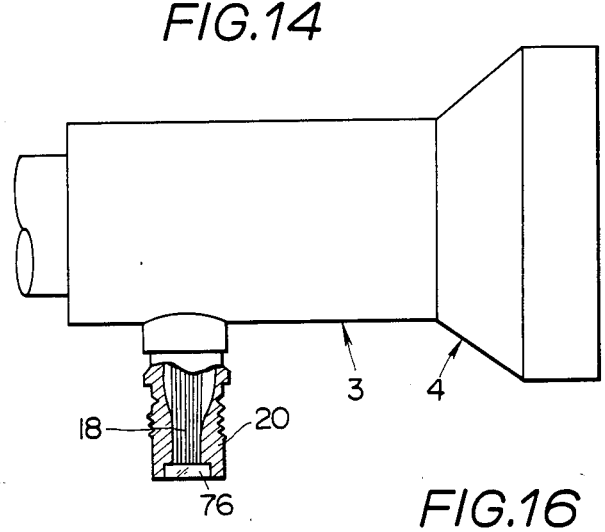

In the example shown in FIG. 14, a light guide cover glass 76 is fitted to the incident end of the light guide 18 of the endoscope 1 shown, for example, in FIG. 1, and is made of borosilicate glass and therefore can be prevented from being fogged at the incident end by the high temperature high pressure water vapor sterilization and reducing the illuminating light transmitting efficiency.

Figures 15, 16:
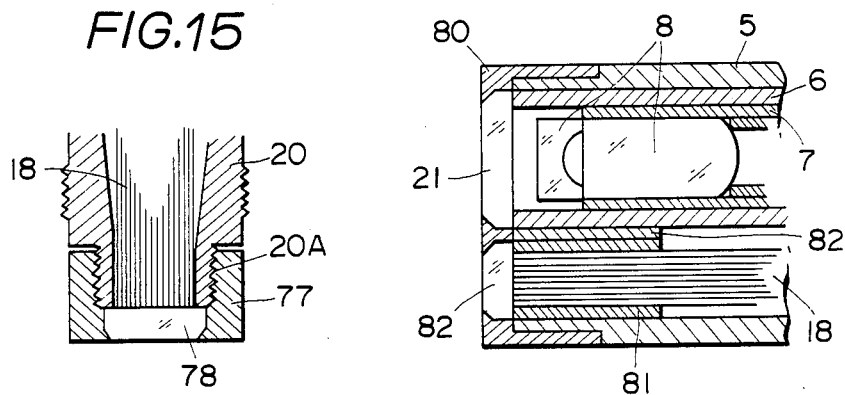

In the example shown in FIG. 15, the light guide mouthpiece 20 shown, for example, in FIG. 1 is steppedly smaller in the diameter on the end side and has a male scew part 20A formed on the outer periphery of the smaller diameter part. On the other hand, a light guide cover glass 78 is fitted in a through hole provided in the part opposed to the incident end surface of the light guide 18 in a cover glass presser 77 in which a female screw thread is formed and threaded to this male screw part 20A. Cover glass 78 is fixed on the outer peripheral surface with a cement. By the way, the cover glass 78 is incised on the peripheral edge of the end surface facing the outside and the cover glass presser 77 in the part opposed to this incision is provided with a flange part so that, when the cover glass presser 77 is threaded to the part 20A, the cover glass 78 may be prevented from escaping and dropping. By the way, the cover glass 78 is made of borosilicate glass.

In this example, before the cover glass presser 77 is fitted, the light guide 18 is ground on the incident surface and then the cover glass presser 77 fitted with the cover glass 78 can be screwed to the mouthpiece 20.

By the way, in the above mentioned example, the cover glass presser 77 may be secured to the mouthpiece by pressing, soldering or brazing instead of screwing.

Figure 17:
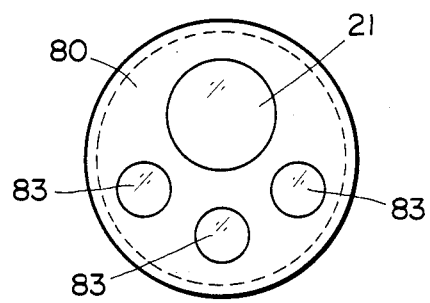

In the example shown in FIGS. 16 and 17, the outer tube 5 is made steppedly smaller in the diameter on the tip side so as to be able to be pressed and secured in a cover glass frame 80. The light guide 18 is bundled on the tip side, for example, with three mouthpieces (one is shown in FIG. 16) and is secured within through holes of a mouthpiece fixing member 82 closing the meniscus-shaped air gap on the tip side of the outer tube 5. The above mentioned outer tube 5, inner tube 6 and mouthpiece 81 are made flush with one another on the tip surfaces. On the end surface on which they are made flush, the objective cover glass 21 and the cover glass frame 80 in which the three light guide cover glasses 83 are secured as shown in the elevation of FIG. 17 are pressed and secured so as to be in contact on the inside end surfaces.

Both of the above mentioned cover glasses 21 and 83 are made of borosilicate glass.

In case the above mentioned cover glass frame 80 is to be fitted, the respective light guides 18 and mouthpiece 81 cut to be flush with the outer tube 5 are ground on the end surfaces and then the cover glass frame 80 fitted with the cover glasses 21 and 83 may be pressed and secured in the outer tube 5. In this example, even if the cover glasses 21 and 83 deteriorate due to the use for a long period, it will be easy to replace them.

By the way, in the present invention, in any other structure than those shown in the above mentioned respective drawings, at least either of an observing optical system and illuminating optical system may be formed and tightly sealed on the end surface facing the outside with cover glasses made of borosilicate glass.

By the way, the transparent closing members fitted to the wide end surface on the above mentioned outside surface are not limited to be cover glasses but may be concave or convex lens-shaped.

By the way, the above mentioned cover glasses are made of borosilicate glass but may be made of any other glass material not deteriorating under a high temperature high pressure water vapor. As shown, for example, in FIG. 15 or 16, the cover glasses easy to replace by removing the cover glass frames may be somewhat endurable to the high temperature high pressure water vapor.

FIGS. 18 to 22 show some modification examples easy to assemble, high in the cementing strength of the cementing part and improved in the sealability.

Figure 18:
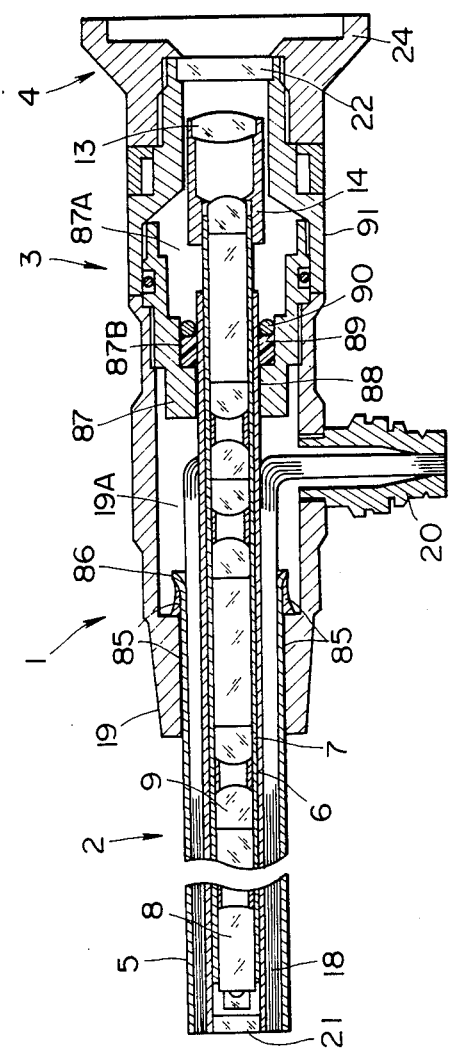
FIGS. 18 to 22 show some modified examples of cementing parts of an endoscope to which the present invention is applied.
Figure 19:
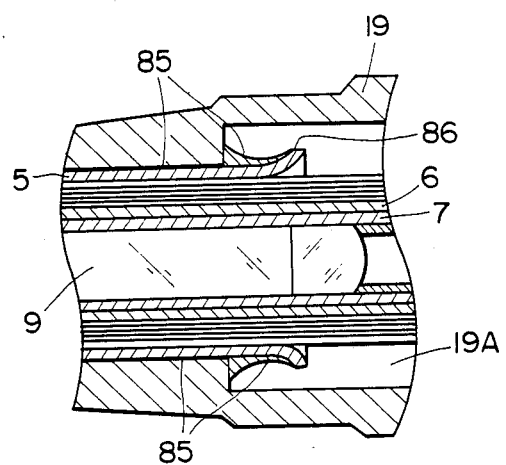

That is to say, in the example shown in FIGS. 18 and 19, the operating part body 19 holding the outer tube 5 is externally fitted at the front end to the outer peripheral part on the rear end side of the outer tube 5 and is cemented liquid tight to the outer tube 5 with a cement 85 such as a solder, adhesive or brazing material. This outer tube 5 is led on the rear end side into the internal space 19A of the above mentioned operating part body 19 and is bent at the rear end peripherally in the outer peripheral direction to form a dam 86 as an outflow preventing means for preventing the above mentioned cement from flowing out. This dam 86 may be formed by arcuately bending the rear end part of the outer tube 5 as shown in FIG. 19 or by bending it, for example, substantially at right angles.

The inner tube 6 inserted through the above mentioned outer tube 5 is cemented with a cement 88 to the front end part of a lens system holding frame 87 screwed inside the operating part body 19. Further, this inner tube 6 is led on the rear end side into the internal space 87A of the above mentioned lens system holding frame 87. On the other hand, a recess 87B corresponding to the outer peripheral part of the above mentioned inner tube 6 is formed inside the above mentioned lens system holding frame 87 and is filled with a cement 89 sealed with an 0-ring so as to be liquid-tight.

An eyepiece part frame 91 is provided and connected to the rear end side of the above mentioned lens system holding frame 87. The eyepiece cover glass 22 is painted with a cement on the periphery and is secured liquid tight to the rear end part of this eyepiece part frame 91. The eyepiece frame 14 holding the eyepiece 13 is secured to the rear end part of the system tube 7.

The operation of the example shown in FIGS. 18 and 19 by the above formation shall be explained in the following.

In assembling the endoscope 1, if the outer tube 5 is cemented to the operating part body 19 with a sufficient amount of the cement 85 interposed in the cementing part, this cement 85 may protrude out of the cementing part of the tube 5 and operating part body 19. According to this example, as the outer tube 5 is led into the internal space 19A of the operating part body 19 and has the dam 86 formed on the outer periphery of the rear end part, the protruded cement 85 will accumulate and set between the cementing part and dam 86. Therefore, the cement 85 will be prevented from expanding inward from the end surface of the outer tube 5 and setting to reduce the inside diameter of the outer tube 5 and the inner tube 6 and light guide fibers 8 will be able to be easily inserted through this outer tube 5.

Also, the outer tube 5 and the operating part body 19 will be cemented with each other even by the cement 85 accumulated between the cementing part of the operating part body 19 with the outer tube 5 and the dam 86, the cementing strength of the outer tube 5 and operating part body 19 will increase and the sealability will be improved by the cement 85 accumulated between the cementing part and dam 86.

In the cementing part of the inner tube 6 and lens system holding frame 87, the cementing strength and sealability are improved by the cement 89 filling the recess 87B of the lens system holding frame 87 and the O-ring 90.

Figure 20:
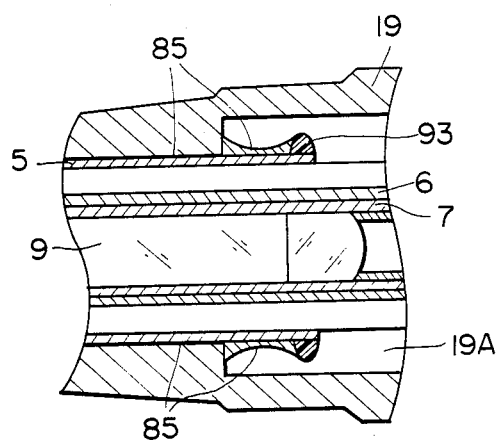

In the example shown in FIG. 20, the outer tube 5 is led in the rear end part into the internal space 19A of the operating part body 19, a dam 93 as an outflow preventing means is peripherally provided by a cement on the outer periphery of the rear end part of this outer tube 5 so that the cement 85 may be prevented by this dam 93 from flowing out.

By the way, the above mentioned dam 93 is not limited to be provided on the outer periphery of the rear end part of the outer tube 5 but may be provided on the outer periphery of the outer tube 5 in the part led into the internal space 19A of the operating part body 19.

According to this example, the outflow preventing means is easier to form than in the example shown in FIG. 19.

Figure 21:
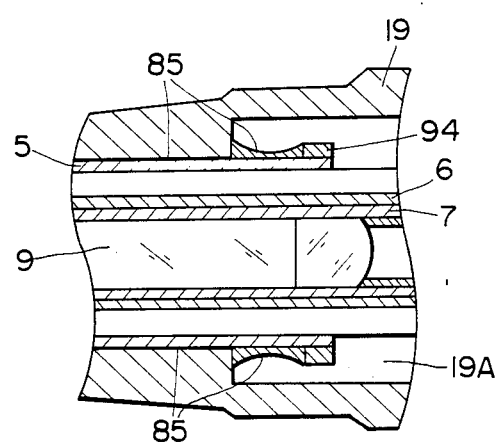

In the example shown in FIG. 21, a ring-shaped member 94 is externally fitted on the outer periphery of the rear end part of the outer tube 5 led into the internal space of the operating part body 19 so as to form an outflow preventing means.

By the way, the above mentioned ring-shaped member 94 may be a cylindrical member such as a metal pipe, a stainless steel pipe or a resin tube such as a thermocontracting tube. Further, this ring-shaped member 94 is not limited to be provided on the outer periphery of the rear end part of the outer tube but may well be provided on the outer periphery of the outer tube 5 in the part led into the internal space 19A of the operating part body 19.

According to this example, the outflow preventing means is easier to form than in the example shown in FIG. 19.

Figure 22:
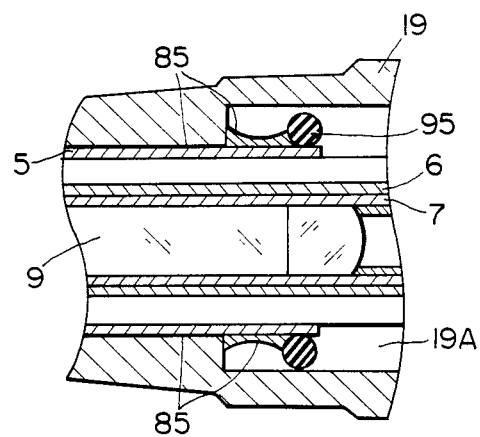

In the example shown in FIG. 22, an O-ring 95 is externally fitted on the outer periphery of the rear end part of the outer tube led into the internal space 19A of the operating part body 19 so as to form an outflow preventing means.

By the way, the above mentioned O-ring 95 may be of any material and is not limited to be provided on the outer periphery of the rear end part of the outer tube 5 but may be provided on the outer periphery of the outer tube 5 in the part led into the internal space 19A of the operating part body 19.

By the way, in the same manner as of the O-ring 90 interposed between the inner tube 6 and lens system holding frame 87, the above mentioned O-ring 95 may be in contact with the outer periphery of the outer tube 5 and the inner periphery of the operating part body 19 so as to improve the sealability.

According to this example, the outflow preventing means is easier to form than in the example shown in FIG. 19.

By the way, the examples of a rigid endoscope have been explained in the modification examples shown in FIGS. 18 to 22 but the same structure of the cementing part can be applied also to a flexible endoscope.

By the way, in an endoscope having not only the outer tube 5 but also, for example, the inner tube 6, forceps channel, air feeding path or water feeding path, such structure of the cementing part as is shown in any of FIGS. 18 to 22 can be applied in cementing the tubular member forming such forceps channel, air feeding path or water feeding path with the holding member holding such tubular member.

FIGS. 23 to 26 show examples of light guide cables connected to the light guide fibers 18 of endoscopes to which the present invention is applied.

That is to say, in the example shown in FIGS. 23 and 24, a light guide cable 101 comprises an elongate flexible light guide cable part 102, a (rigid) endoscope side connector 105 formed in one end part of this light guide cable part 102 and connectable to the light guide connector 20 of the endoscope 1 and a light source side connector 107 formed in the other end part of this light guide cable part 102 and connectable to a light source device 106.

An illuminating lamp not illustrated is contained within the light source device 106 to which the light source side connector 107 is connected so that illuminating lights may be collected and projected onto the incident end surface of the connected connector 107 by a light collecting lens. The thus collected and projected illuminating light is transmitted to the endoscope 1 side through the light guide cable 101 so as to be able to be projected toward an object out of a light guide projecting end at the tip of the insertion part 2.

Now, as shown in FIG. 24, the light guide cable part 102 of the light guide cable 101 is coated with a silicone tube 112. A net tube (blade) 113 formed by knitting fibers and a spiral tube (flex) 114 formed by spirally winding a band-shaped metal are internally fitted inside this silicone tube 112. A light guide fiber bundle 115 is inserted through this spiral tube 104.

The above mentioned light guide fiber bundle 115 is secured at one end within a through hole of the endoscope side connector 105 and the light source side connector 107 to which the light guide fiber bundle 115 is secured at the light source side end is of such structure as is shown in FIG. 24.

This connector 107 comprises a mouthpiece part 121 fitted to a mouthpiece receiver of the light source device 106, a connecting frame 122 connected to this mouthpiece part 121 by soldering or brazing and a grip part 123 screwed to the screw part of this connecting frame 122.

The light guide fiber bundle 115 inserted through the above mentioned spiral tube 114 is bound and secured on the end side within a pipe 124 which is passed through a through hole of the grip part 123 and is fitted and secured within a through hole of the connecting frame 122. It is a feature that the length part LA substantially from the end of the light guide fiber bundle 115 bundled and secured within this pipe 124 is made a heatproof cemented zone (heatproof secured zone) 115A by a heatproof glass resin cement and the length part LB substantially adjacent to this heatproof cemented zone 115 is made a waterproof cemented zone 115B by water vapor and waterproof epoxy resin or the like so that any water vapor coming in through the silicone tube 112 or the like on the rear part side may be prevented by this waterproof cemented zone from entering the end side of the front part.

By the way, the above mentioned heatproof cemented zone 115A is secured by pouring the glass resin from the end surface side and, on the other hand, the waterproof cemented zone 115B by the water vaporproof and waterproof epoxy resin is formed by pouring the above mentioned epoxy resin through a hole 125 made in the course of the pipe 124.

A rod lens 126 fitted and secured in the through hole of the mouthpiece part 121 is in front of the end surface of this fiber bundle 115, the inside diameter of the front end of the mouthpiece part 121 in front of this rod lens 126 is enlarged to fit a cover glass 127 and this fitting part is secured with a heatproof cement.

An O-ring 128 is annularly fitted in a peripheral groove formed in the through hole of the mouthpiece part 121 in the part in which the above mentioned rod lens 126 is fitted so as to be watertight and airtight. Therefore, even if a water vapor comes in through the cement securing the cover glass 127, it will be prevented by the O-ring 128 from entering the inner part and deteriorating the end surface of the fiber bundle 115.

Now, the spiral tube 114 covering the outer periphery of the fiber bundle 115 is fitted in the end part into the through hole of the connecting frame 122 and is secured with a cement or the like. The net tube 113 covering the outer periphery of this spiral tube 114 and the silicone tube 112 on the outer periphery of this net tube 122 are externally fitted to the small diameter part at the rear end of the connecting frame 122, are secured with a cement or the like and are covered on the outer periphery with the grip part 123.

Thus, in this example, the rod lens 126 is provided on the front part side of the end surface of the light guide fiber bundle 115 and the O-ring 128 is interposed between the outer periphery of this rod lens 126 and the inner periphery of the mouthpiece part 121 so that, for example, in the case of the high pressure steam sterilization, the water vapor may be prevented from coming in. Further, the cover glass 127 is secured with a cement. Also, as the heatproof cemented zone 115A and waterproof cemented zone 115B are formed near the end of the light guide fiber bundle 115, even if a water vapor comes in through the silicone tube 112, net tube 113 and spiral tube 114, the water vapor will be prevented by the waterproof cemented zone 115B from entering the end side through the air gap or the like of the adjacent fibers. Therefore, the water vapor will be prevented from reaching the end surface of the fiber bundle 115 and therefore the end surface will not be deteriorated with the water vapor. By the way, the pipe 124 is secured on the outer periphery in the same manner in the cemented zones 115A and 115B.

In the example shown in FIG. 25, in the connector 131, a cover glass 132 is secured in front of the end surface of the fiber bundle 115 without using the rod lens 126 in the example shown in FIG. 24. An O-ring 133 is annularly fitted in a peripheral groove formed on the outer periphery of this cover glass 132 so that the structure may be watertight and airtight. By the way, such heatproof cemented zone 115A' of a length LA' and waterproof cemented zone 115B' of a length LB' as are, for example, in the example shown in the above mentioned FIG. 24 are formed near the end of the light guide fiber bundle 115.

The functions and effects of this example are substantially the same as in the above mentioned FIG. 24.

In the example shown in FIG. 26, in the connector 141, the length LB of the waterproof cemented zone B is made larger to form a waterproof cemented zone 115C of a length LC.

A hygroscopic agent 142 is contained in a ring-shaped air gap provided on the inner peripheral wall of the connecting part 122 in the course of this waterproof cemented zone 115 and can be contained through a hole 143 communicating with the outside and closed with a glass plug after the hygroscopic agent is contained. Such moisture absorption indicating agent varies in color by moisture absorption and cobalt chloride is mixed in the hygroscopic agent 142 so that the degree of moisture absorption may be known through the glass plug.

By the way, in the pipe 124, holes 144 are locally provided in the part in which the hygroscopic agent 142 is on the outer periphery so that the inside fiber bundle 115 may be exposed through the holes 144. The others are the same as in the example shown in the above mentioned FIG. 24.

Under the ordinary using condition, the entry of a water vapor can be prevented by the waterproof cement but, in case the endoscope is used over a very long period or is severely used, even if a slight amount of a water vapor comes in, according to this example, the moisture will be absorbed by the hygroscopic agent and the water vapor will be able to be positively prevented from reaching the end surface side. In case the moisture absorption amount becomes above a proper value, the glass plug may be broken and the inside hygroscopic agent 142 may be sucked out and replaced with a new hygroscopic agent.

By the way, the heatproof cement is not limited to the glass resin but may be any other cement endurable to the heat of the collected light.

Also, the water vaporproof cement is not limited to the epoxy resin but may be any other cement which is water vapor-proof.

The formation of such light guide cable as is shown in any of FIGS. 23 to 26 can be applied not only to medical endoscopes but also to industrial endoscopes or any others than endoscopes.

By the way, the endoscope side connector is not limited to be formed in both cemented zones but may be merely secured with the watervaporproof cement.

FIG. 27 shows the second embodiment of the present invention.

In this embodiment, the eyepiece frame 14 is provided with a ventilating hole 25 and the spaces between the objective 8 and system tube 7 and between the relay lens 9 end part and relay lens presser 33 pressing it are sealed respectively with the cements 10 and 2 so that the part of the observing optical system from the objective 8 to the relay lens end part may be airtight. The other formations are the same as of the first embodiment shown in FIG. 1.

In such formation, even if a water vapor enters the endoscope 1, the water vapor will be prevented from entering the observing optical system from the objective 8 to the relay lens 9. As air moves into and out of the internal space of the eyepiece frame 14 and the space between the eyepiece frame 14 and operating part body 19, the humidity will not become particularly high in the internal space of the above mentioned eyepiece frame 14 and fogging will be prevented from occurring inside the eyepiece 13 and on the relay lens 9 end surface.

Also, in this embodiment, no O-ring is required to be provided between the relay lens frame 11 and connecting tube 12 and between the connecting tube 12 and eyepiece frame 14 and the assembling work is simple.

By the way, the above mentioned ventilating hole 25 may be plural.

As shown in FIG. 28, the endoscope body 19 may be provided with a ventilating hole 28 and a plug 29 sealing this ventilating hole 28 so that, in case a water vapor enters the endoscope body 1, the above mentioned plug may be opened and dry air may be fed into the endoscope 1 through the ventilating hole 28 to dry the interior of the endoscope 1.

The other functions and effects are the same as of the first embodiment.

Figure 29:
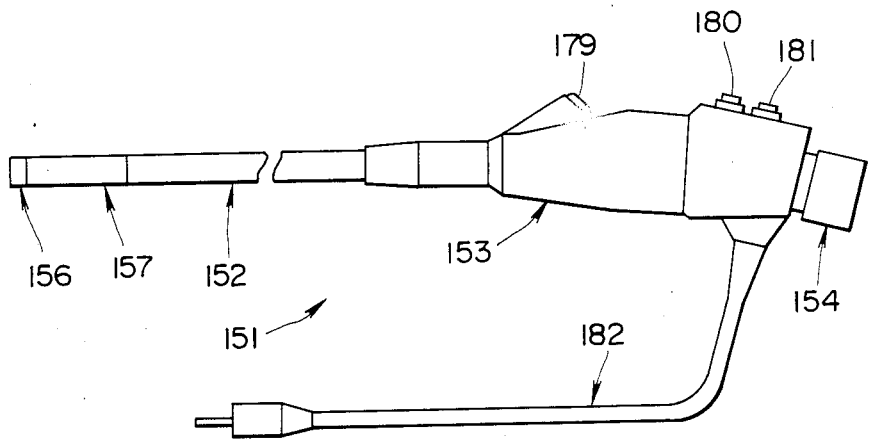
FIGS. 29 and 30 show the third embodiment of the present invention.
Figure 30:
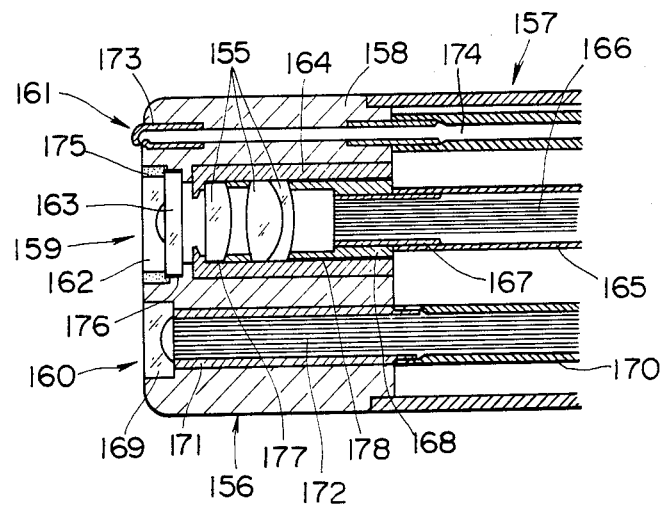

FIGS. 29 and 30 show the third embodiment of the present invention.

In this embodiment, the present invention is applied to a flexible embodiment in which an image guide consisting of a fiber bundle is used for the observing optical system.

In the drawings, a flexible endoscope 151 is formed of an elongate flexible insertion part 152, a large diameter operating part 153 airtightly secured to the rear end of this insertion part 152 and an eyepiece part 154 conneced to the rear end of this operating part and is entirely of an airtight structure.

In the above mentioned insertion part 152, as shown in FIG. 30, a rigid tip forming part 156 containing an objective system 155 and others and a curvable part 157 which can be curved are provided as connected in turn from the tip side.

In the above mentioned tip forming part 156, an observing window 159, illuminating window 160, air and water feeding port 161 and forceps port not illustrated are provided in the tip surface part of the tip forming part body 158. The above mentioned observing window 159 is provided with a cover lens 162. A filter 163 and the above mentioned objective system 155 held by a lens frame 164 are provided as connected in the rear of the cover lens 162. An image guide 166 coated with a soft tube 165 is so arranged that its tip surface may be located in the image forming position of this objective system 155. The tip side bundled and fixed by a mouthpiece 167 of the image guide 166 is fixed within the above mentioned lens frame 164 through a spacer 168.

On the other hand, the above mentioned illuminating window 160 is provided with a cover lens 169 for illumination. A light guide 172 coated with a soft tube 170 and bundled by a mouthpiece 171 on the tip side is provided as connected in the rear of this cover lens 169.

Further, the above mentioned air and water feeding port 161 is provided with an injection nozzle 173 opening toward the above mentioned observing window 159 and illuminating window 160 and communicating with an air and water feeding path 174 provided within the insertion part 152.

In this embodiment, the space between the above mentioned cover lens 162 and tip forming part body 158 and the space between the above mentioned filter 163 and tip forming part body 158 are kept airtight respectively by cements 175 and 176 and also the space between the above mentioned objective system 155 and lens frame 164 and the space between the above mentioned spacer 168 and lens frame 164 are kept airtight respectively by cements 177 and 178.

By the way, in the drawing, the reference numeral 179 represents a forcepts inserting port, 18 represents an air and water feeding button, 181 represents a suction button and 182 represents a light guide cable.

In such formation, even if a water vapor enters the interior from the cover lens 162 side, the water vapor will be prevented from entering the above mentioned objective system 155, fogging will be prevented from occurring within the objective system 155 and the repair is simple.

FIG. 31 shows the fourth embodiment of the present invention.

In this embodiment, a cylindrical hygroscopic member 192 formed of cellophane as a sheet-shaped hygroscopic material wound, for example, by about 20 to 30 rounds on the outer periphery of the connecting tube 12, fixed at the end with a cement or the like and having a flexibilty is provided in the space between the operating part body 19 and connecting tube 12. The above mentioned cellophane is of viscose made film-like, is one of regenerated cellulose consisting primarily of cellulose hydrates which are highly hygroscopic and is.

The other formations are substantially the same as of the first embodiment shown in FIG. 1.

In this embodiment, the interior of the endoscope is kept airtight and liquid tight by a cement or the like. However, the high molecular weight substance used for the cement or the like has itself a hygroscopicity so as to discharge a moisture within the dry endoscope when the moisture absortion amount reaches a fixed amount. When used for a long period, the cement or the like will deteriorate and therefore the entry of a moisture into the endoscope will be unavoidable. Particularly, in the high pressure steam sterilization, as a high temperature high pressure water vapor is used, the water vapor is very likely to come in.

In this embodiment, such water vapor entering the interior is absorbed by the hygroscopic member cellophane 192 formed of cellulose hydrate and the interior is kept at a low humidity, therefore, after the sterilization, even if the normal temperature is returned, the water vapor will not frost and no frosting will obstruct the observation and corrode the component members within.

By the way, the water vapor coming in from the objective side passes between the inner tube 6 and system tube 7, reaches the interior or the operating part body 19 and is absorbed by the above mentioned hygroscopic member 24.

Also, the hygroscopic cellophane member 192 formed of cellulose hydrate will not be broken by the deterioration or the like to produce broken pieces and therefore a favorable observation visual field is always secured.

Such flexible sheet-shaped hygroscopic material as cellophane can be easily shaped to be of any form, therefore can be internally fitted without modifying the respective member forms of the endoscope, can be easily cut or worked to be of any size as required, therefore can be improved in the workability and is so cheap as to be able to reduce the production cost.

FIG. 32 is a view partly in section of the tip part of the endoscope according to the fifth embodiment of the present invention.

This embodiment, substantially the same as in the forth embodiment, comprising an endoscope wherein a hygroscopic cellophane member is provided in the space between the operating part body and connecting tube, a hygroscopic member is provided also on the objective side.

In the drawing, the light guide fibers 18 are inserted between the outer tube 5 and inner tube 6. Inside the tip part of the inner tube 6, a calked frame 201 to which the objective cover glass 21 is connected and fixed is secured by such means as soldering so as to be airtight and liquidtight between the objective cover glass 21 and calked frame 201 and between the calked frame 201 and inner tube 6.

The system tube 7 is inserted through the above mentioned inner tube 6. The same as in the fourth embodiment, the objective 8 and the relay lens 9 not illustrated are internally fitted within this system tube 7.

In this embodiment, a hygroscopic cellophane member 203 is formed by winding a sheet of cellulose hydrate, for example, by about five rounds on the outer peripheray of a front objective 202 provided at the tip of the above mentioned objective 8 and cylindrically fixed by a cement is cemented to the above mentioned objective 8.

In case the hygroscopic member 192 is provided only on the eyepiece side (for example, between the operating part body 19 and connecting tube 12) as shown in the fourth embodiment, a water vapor coming in from the objective side will pass between the inner tube 6 and system tube 7, will reach the interior of the operating part body 19 and will be absorbed by the above mentioned hygroscopic member 192 but an extremely slight amount of the water vapor will be likely to remain between the above mentioned inner tube 6 and system tube 7. According to this embodiment, the water vapor coming in from the objective side is absorbed by the above mentioned hygroscopic member 203 and therefore the interior of the endoscope can be kept at a low humidity.

The other functions and effects are the same as of the fourth embodiment.

By the way, in case the space within the endoscope body is extremely narrow and a sufficient amount of cellophane can not be internally fitted or in case a more positive hygroscopicity and the long use of the endoscope are required, the following modifications may be made:

(a) In FIG. 31, a O-ring or the like keeping airtightness and liquidtightness is provided between the operating part body 19 and eyepiece cover glass 22 or the number of the provided O-rings is increased.

(b) In FIG. 31, the sheet-shaped cellulose hydrate, cellophane material is wound also on the eyepiece frame 14.

(c) In FIG. 32, the system tube 7 is made shorter on the tip side, the objective lens 8 is exposed in a part of the tip side from the system tube 7 and the hygroscopic cellophane is wound directly on this part.

In the above mentioned embodiment, cellophane is used as a flexible sheet-shaped hygroscopic cellulose hydrate material but the hygroscopic material is not limited to be cellophane but may be blotting paper which is porous cellulose fiber paper, Japanese paper or the like.

The hygroscopic member is not limited to be provided in the place mentioned in the above mentioned embodiments but may be provided in any part within the endoscope.

The hygroscopic member formed of a flexible sheet-shaped hygroscopic material may be provided within an endoscope body of no particularly airtight or liquidtight structure.

By the way, in the fourth and fifth embodiments, the relay lens 9 is used for the observing optical system but image guide fibers may be used.

The above mentioned fourth and fifth embodiments are examples as applied to a rigid endoscope but the present invention can be applied in the same manner to a flexible endoscope or the like.

Further, the present invention is not limited to the above described first to fifth embodiments but can be applied also to a rigid endoscope or the like wherein, for example, an image guide consisting of a fiber bundle is used for the observing optical system.

It is apparent that, working modes which differ in a wide range from the embodiments disclosed herein can be formed on the basis of this invention without deviating from the spirit and scope of the invention. This invention is not restricted by its specific working modes except to the extent that the same may be limited by the appended claims.

What is claimed is:

1. An endoscope comprising:
    an endoscope body having an elongate insertion part having an observing window at the tip and an operating part provided as connected to the rear end of said insertion part;
    a first airtightening means for making said endoscope body airtight in the structure;
    an observing optical system provided within said endoscope body and transmitting an observed image from the tip of said insertion part to said operating part; and
    a second airtightening means for making at least a part of said observing optical system airtight in the structure.

2. An endoscope according to claim 1 wherein said insertion part is rigid.

3. An endoscope according to claim 1 wherein said first airtightening means is cementing with a cement.

4. An endoscope according to claim 1 wherein said first airtightening means is cementing with a cement and an O-ring.

5. An endoscope according to claim 1 wherein said second airtightening means is cementing with a cement.

6. An endoscope according to claim 1 wherein said second airtightening means is cementing with a cement and an O-ring.

7. An endoscope according to claim 2 wherein said observing optical system comprises an objective provided within the tip part of said insertion part, an eyepiece provided within said operating part and a relay lens connecting said objective and eyepiece with each other.

8. An endoscope according to claim 7 wherein said objective and relay lens are contained in a system tube, said eyepiece is held in an eyepiece frame and said system tube and eyepiece frame are connected with each other.

9. An endoscope according to claim 7 wherein the observing optical system from said objective to said eyepiece is made airtight in the structure by said second airtightening means.

10. An endoscope according to claim 7 wherein the observing optical system from said objective to said relay lens is made airtight in the structure by said second airtightening means.

11. An endoscope according to claim 8 wherein the observing optical system from said objective to the end of said relay lens is made airtight in the structure by said second airtightening means and said eyepiece frame between said relay lens end and said eyepiece is provided with a ventilating hole.

12. An endoscope according to claim 11 wherein said endoscope body is provided with a ventilating hole and plug sealing said ventilating hole.

13. An endoscope according to claim 1 wherein said insertion part is flexible.

14. An endoscope according to claim 13 wherein said observing optical system has an objective system and an image guide consisting of a fiber bundle inserted through said insertion part, arranged on the tip surface in an image forming position of said objective system and transmitting an image formed by said objective to said operating part.

15. An endoscope according to claim 14 wherein said objective system is made airtight in the structure by said second airtightening means.

16. An endoscope comprising:
 an endoscope body having an elongate insertion part having an observing window at the tip and an operating part provided as connected to the rear end of said insertion part;
 an observing optical system provided within said endoscope body and transmitting an observed image from the tip of said insertion part to said operating part; and
 a hygroscopic member provided within said endoscope body and formed of a flexible sheet-shaped hygroscopic material.

17. An endoscope according to claim 16 wherein said endoscope body is made airtight in the structure.

18. An endoscope according to claim 16 wherein said sheet-shaped hygroscopic material is cellophane hydrate.

19. An endoscope according to claim 16 wherein said sheet-shaped hygroscopic material is blotting paper.

20. An endoscope according to claim 16 wherein said sheet-shaped hygroscopic material is Japanese paper.

21. An endoscope according to claim 16 wherein said insertion part is rigid.

22. An endoscope according to claim 16 wherein said observing optical system comprises an objective provided within the tip part of said insertion part, an eyepiece provided within said operating part and a relay lens connecting said objective and eyepiece with each other.

23. An endoscope according to claim 22 wherein said objective and relay lens are contained in a system tube, said eyepiece is held in an eyepiece frame and said system tube and eyepiece frame are connected with each other.

24. An endoscope according to claim 23 wherein the observing optical system from said objective to said eyepiece is made airtight in the structure.

25. An endoscope according to claim 23 wherein said system tube and said eyepiece frame are connected with each other through a connecting tube and said hygroscopic member is formed of said sheet-shaped hygroscopic material wound on the outer periphery of said connecting tube.

26. An endoscope according to clim 23 wherein a part of said objective is projected on the tip side from said system tube and said hygroscopic member is formed of said sheet-shaped hygroscopic material wound on the outer periphery of the projected part of said objective.

* * * * *